US011872051B2

(12) United States Patent
D'Lima et al.

(10) Patent No.: US 11,872,051 B2
(45) Date of Patent: Jan. 16, 2024

(54) SHOULDER MONITORING AND TREATMENT SYSTEM

(71) Applicant: ACTIVE4D, INC., Rancho Santa Fe, CA (US)

(72) Inventors: Darryl D'Lima, San Diego, CA (US); Heinz Hoenecke, San Diego, CA (US); David G. Matsuura, Del Mar, CA (US)

(73) Assignee: ACTIVE4D, INC., Rancho Santa Fe, CA (US)

( * ) Notice: Subject to any disclaimer, the term of this patent is extended or adjusted under 35 U.S.C. 154(b) by 259 days.

(21) Appl. No.: 17/320,954

(22) Filed: May 14, 2021

(65) Prior Publication Data

US 2021/0267537 A1 Sep. 2, 2021

Related U.S. Application Data

(62) Division of application No. 15/508,871, filed as application No. PCT/US2015/048561 on Sep. 4, 2015, now Pat. No. 11,064,936.

(Continued)

(51) Int. Cl.
*A61B 5/00* (2006.01)
*A61B 5/11* (2006.01)
(Continued)

(52) U.S. Cl.
CPC ............. *A61B 5/4576* (2013.01); *A61B 5/11* (2013.01); *A61B 5/1121* (2013.01); *A61B 5/389* (2021.01); *A61B 5/4519* (2013.01); *A61B 5/4833* (2013.01); *A61B 5/4842* (2013.01); *A61B 5/6824* (2013.01); *A61B 5/6831* (2013.01); *A61B 5/6833* (2013.01);
(Continued)

(58) Field of Classification Search
CPC ....... A61B 5/4576; A61B 5/11; A61B 5/1121; A61B 5/389; A61B 5/4519; A61B 5/4833; A61B 5/4842; A61B 5/6824; A61B 5/6831; A61B 5/6833; A61B 5/7475; A61B 2505/09; A61F 5/3738
See application file for complete search history.

(56) References Cited

U.S. PATENT DOCUMENTS

| 5,513,651 A | 5/1996 | Cusimano et al. |
| 5,724,984 A * | 3/1998 | Arnold .................... A61B 5/25 600/382 |

(Continued)

FOREIGN PATENT DOCUMENTS

| EP | 2666410 A1 | 11/2013 |
| JP | 2007050033 A | 3/2007 |

OTHER PUBLICATIONS

Office Action dated Jul. 7, 2022 in European Patent Application No. 15838630.0.

*Primary Examiner* — May A Abouelela
(74) *Attorney, Agent, or Firm* — Procopio, Cory, Hargreaves & Savitch LLP

(57) ABSTRACT

A system and method is used to monitor, control, and/or provide feedback relative to one or more factors related to a patient's body, such as a shoulder, pursuant to a treatment process. The system monitors, controls, and/or provides feedback relative to shoulder factors including shoulder motion, shoulder muscle contraction, and external pressure on the shoulder.

18 Claims, 13 Drawing Sheets

Related U.S. Application Data

(60) Provisional application No. 62/182,457, filed on Jun. 20, 2015, provisional application No. 62/046,014, filed on Sep. 4, 2014.

(51) Int. Cl.
*A61B 5/389* (2021.01)
*A61F 5/37* (2006.01)

(52) U.S. Cl.
CPC .......... *A61B 5/7475* (2013.01); *A61F 5/3738* (2013.01); *A61B 2505/09* (2013.01)

(56) References Cited

U.S. PATENT DOCUMENTS

| | | | | |
|---|---|---|---|---|
| 5,916,172 A * | 6/1999 | Hodges | ................ | A61B 5/389 600/595 |
| 6,050,962 A * | 4/2000 | Kramer | ................ | G06F 3/011 600/595 |
| 6,122,544 A * | 9/2000 | Organ | ................ | A61B 5/0531 600/547 |
| 6,564,079 B1 * | 5/2003 | Cory | ................ | A61B 5/282 600/397 |
| 6,654,626 B2 * | 11/2003 | Devlin | ................ | A61B 5/291 600/397 |
| 6,751,493 B2 * | 6/2004 | Wenger | ................ | A61B 5/282 600/382 |
| 6,973,343 B2 * | 12/2005 | Wenger | ................ | A61B 5/282 600/382 |
| 7,616,980 B2 * | 11/2009 | Meyer | ................ | A61B 5/282 600/382 |
| 8,238,996 B2 * | 8/2012 | Burnes | ................ | A61B 5/282 600/382 |
| 8,442,615 B2 * | 5/2013 | David | ................ | A61B 5/341 600/387 |
| 2004/0054273 A1 * | 3/2004 | Finneran | ................ | A61B 5/30 600/546 |
| 2004/0204656 A1 * | 10/2004 | Tolvanen-Laakso | ................ | A61B 5/296 600/546 |
| 2005/0215916 A1 * | 9/2005 | Fadem | ................ | A61B 5/30 600/509 |
| 2007/0148624 A1 * | 6/2007 | Nativ | ................ | A63B 24/0006 434/258 |
| 2007/0167859 A1 * | 7/2007 | Finneran | ................ | A61B 5/296 600/546 |
| 2007/0191728 A1 * | 8/2007 | Shennib | ................ | A61B 5/389 128/903 |
| 2008/0108909 A1 * | 5/2008 | Reger | ................ | A61B 5/389 600/546 |
| 2008/0243265 A1 * | 10/2008 | Lanier | ................ | A61F 2/583 600/587 |
| 2008/0275309 A1 * | 11/2008 | Stivoric | ................ | A61B 5/411 600/300 |
| 2009/0076559 A1 * | 3/2009 | Libbus | ................ | A61N 1/3987 607/6 |
| 2009/0201172 A1 * | 8/2009 | Edell | ................ | A61B 5/0002 600/300 |
| 2009/0209878 A1 * | 8/2009 | Sanger | ................ | A61B 5/389 600/546 |
| 2009/0326406 A1 * | 12/2009 | Tan | ................ | G06F 3/017 341/20 |
| 2010/0152602 A1 * | 6/2010 | Ross | ................ | A61B 5/291 600/546 |
| 2010/0228113 A1 * | 9/2010 | Solosko | ................ | A61N 1/048 600/382 |
| 2011/0071418 A1 * | 3/2011 | Stellar | ................ | A61B 5/4519 600/546 |
| 2011/0118621 A1 * | 5/2011 | Chu | ................ | A61B 5/11 600/587 |
| 2011/0152987 A1 | 6/2011 | Wahlgren et al. | | |
| 2011/0245702 A1 * | 10/2011 | Clark | ................ | G01R 5/28 600/523 |
| 2012/0071743 A1 * | 3/2012 | Todorov | ................ | A61B 5/486 600/372 |
| 2012/0143032 A1 * | 6/2012 | Cyphery | ................ | A61B 5/296 600/382 |
| 2012/0172745 A1 * | 7/2012 | Miyazaki | ................ | A61B 5/389 607/48 |
| 2012/0245439 A1 * | 9/2012 | Andre | ................ | A61B 5/0022 600/595 |
| 2012/0245483 A1 * | 9/2012 | Lundqvist | ................ | A61B 5/296 600/546 |
| 2013/0281795 A1 * | 10/2013 | Varadan | ................ | A61B 7/04 977/762 |
| 2014/0135593 A1 * | 5/2014 | Jayalth | ................ | A61B 5/318 600/301 |
| 2014/0148725 A1 * | 5/2014 | Cadwell | ................ | A61B 5/296 600/546 |
| 2014/0163412 A1 * | 6/2014 | Jacobson | ................ | A61B 5/11 600/546 |
| 2014/0364701 A1 * | 12/2014 | Masakov | ................ | A61B 5/24 600/483 |
| 2015/0004581 A1 * | 1/2015 | Selman | ................ | G09B 19/0038 434/257 |
| 2015/0019135 A1 * | 1/2015 | Kacyvenski | ................ | A61B 5/389 702/19 |
| 2015/0125837 A1 * | 5/2015 | Zhang | ................ | A61B 5/6831 434/258 |
| 2015/0165269 A1 * | 6/2015 | Herrala | ................ | A61B 5/389 482/8 |
| 2015/0309563 A1 | 10/2015 | Connor | | |
| 2016/0135709 A1 * | 5/2016 | Jörg | ................ | A61B 5/6825 600/382 |

* cited by examiner

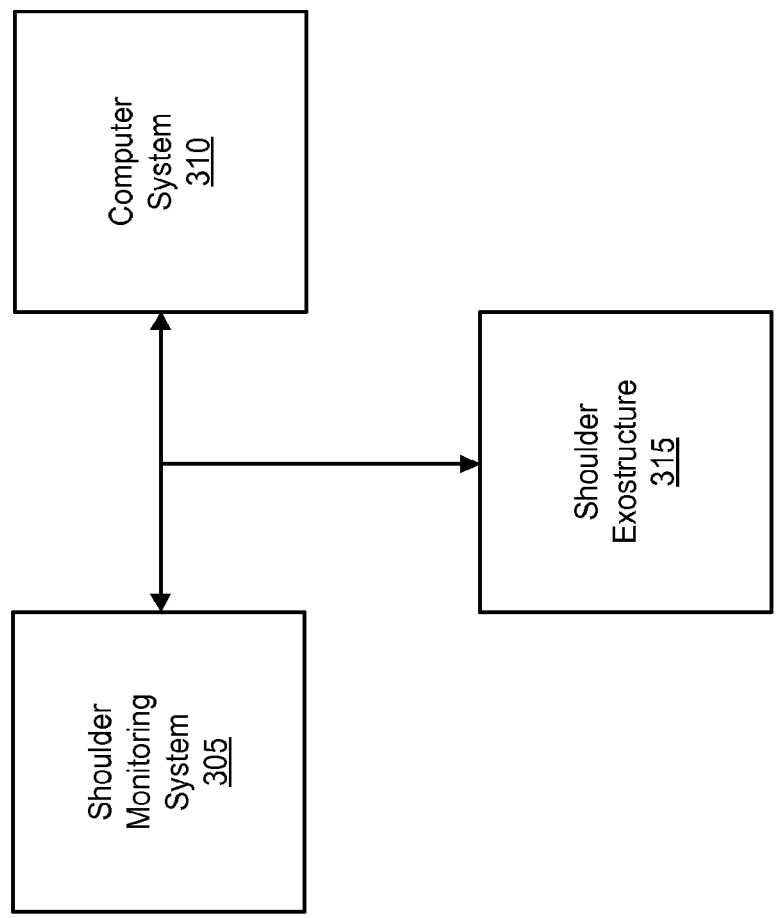

SHOULDER MONITORING AND TREATMENT SYSTEM

RELATED APPLICATIONS

The present application is a divisional of U.S. patent application Ser. No. 15/508,871, filed on Mar. 3, 2017, which is a national stage entry, filed under 35 U.S.C. § 371, of International Application No. PCT/US2015/048561, filed on Sep. 4, 2015, and claims priority to the following U.S. Provisional Patent Applications: (1) U.S. Provisional Patent Application Ser. No. 62/046,014 entitled "Shoulder Monitoring and Treatment System" and filed Sep. 4, 2014; and (2) U.S. Provisional Patent Application Ser. No. 62/182,457 entitled "Shoulder Monitoring and Treatment System" and filed Jun. 20, 2015. The provisional applications are incorporated herein by reference in their entirety and priority to the aforementioned filing dates is claimed.

BACKGROUND

The human shoulder joint is a complex region of the body that has to satisfy several demands such as mobility, stability, and strength. These demands may often conflict with one another and can result in shoulder problems. With reference to FIG. 1, the shoulder joint generally includes the humerus bone which articulates with the scapula bone. The scapula is connected via muscles and ligaments to the thorax. This combined thoraco-scapulo-humeral assembly is commonly referred to as "the shoulder" although the shoulder may include additional elements not described or shown herein.

Shoulder problems may vary and may include, for example, diseases that affect the soft-tissues such as "frozen" shoulder or pericapsulitis, tears of tendons such as the commonly occurring "rotator cuff tear", injuries to the joint such as "labral tears", and arthritis of the glenohumeral articulation. A common theme underlying most shoulder problems is pain and loss of active and passive motion of the shoulder.

Treatment and rehabilitation for shoulder problems may require only non-invasive methods such as physical therapy, or in some cases a combination of invasive methods (i.e. surgery) and non-invasive methods. Traditional methods of rehabilitation for shoulder problems can span several months if not years. The methods of rehabilitation for a patient involve supervised and unsupervised activities and exercises based upon instructions specified by the surgeon, physician, or physical therapist. However, traditional methods have varying levels of success due to various reasons including the absence of reliable methods and devices for monitoring and keeping track of a patient's shoulder motion, relevant muscle activity, and reaction forces around the shoulder during the treatment process.

SUMMARY

Disclosed herein is a system and method that is used to monitor, control, provide feedback, and/or provide historical data analysis and reporting regarding one or more factors related to a patient's shoulder pursuant to a treatment process for shoulder problems. The system monitors, controls, and/or provides feedback relative to shoulder factors including shoulder motion, shoulder muscle contraction, and external pressure on the shoulder. The feedback, which can be in the form of visual, audio, and/or electronic data, is provided in real time and/or stored for review and analysis over a desired period of time. The feedback is provided locally or remotely over a communication network to a user, which can be party interested in the care and outcome of the rehabilitation process, and can include, for example, the patient, a healthcare provider such as a treating physician or a therapist, or a payor responsible for some or all of the cost of treatment. By monitoring and/or controlling relevant parameters of shoulder function, the user can assess progress and recovery, document compliance, predict complications, and tailor the rehabilitation program in accordance with the specific circumstances of the shoulder's condition throughout the recovery.

In one aspect, there is disclosed a shoulder analysis system, comprising: a patch or wearable device having a front side and a back side, the patch sized and shaped to be positioned on shoulder region of a wearer; at least one sensor on the patch, the at least one sensor configured to sense an element associated with the shoulder; a communication component on the patch, the communication component configured to communicate a signal to and from the system; and an attachment element that secures at least a portion of the back side of the band to skin of the wearer; wherein the patch includes at least one opening that provides a visual line of sight through the patch when the patch is positioned on a wearer's shoulder The details of one or more variations of the subject matter described herein are set forth in the accompanying drawings and the description below. Other features and advantages of the subject matter described herein will be apparent from the description and drawings, and from the claims.

BRIEF DESCRIPTION OF THE DRAWINGS

FIG. 3 shows a schematic representation of a shoulder monitoring and treatment system.

DETAILED DESCRIPTION

Before the present subject matter is further described, it is to be understood that this subject matter described herein is not limited to particular embodiments described, as such may of course vary. It is also to be understood that the terminology used herein is for the purpose of describing a particular embodiment or embodiments only, and is not intended to be limiting. Unless defined otherwise, all technical terms used herein have the same meaning as commonly understood by one skilled in the art to which this subject matter belongs.

Disclosed herein is a system and method that is used to monitor, control, and/or provide feedback relative to one or more factors related to a patient's shoulder pursuant to a treatment process for shoulder problems. The system monitors, controls, and/or provides feedback relative to shoulder factors including shoulder motion, shoulder muscle contraction, and external pressure on the shoulder. The feedback, which can be in the form of visual, audio, and/or electronic data, is provided in real time and/or stored for review and manipulation over a period of time. The feedback is provided locally or remotely (over a communications network) to a user, which can be for example, the patient, a healthcare provider such as a treating physician, therapist, or a payor. By monitoring and/or controlling relevant parameters of shoulder function, the user can assess progress and recovery, document compliance with prescribed treatment, predict complications, and tailor the rehabilitation programs in accordance with the shoulder's state of recovery.

Figure 1:
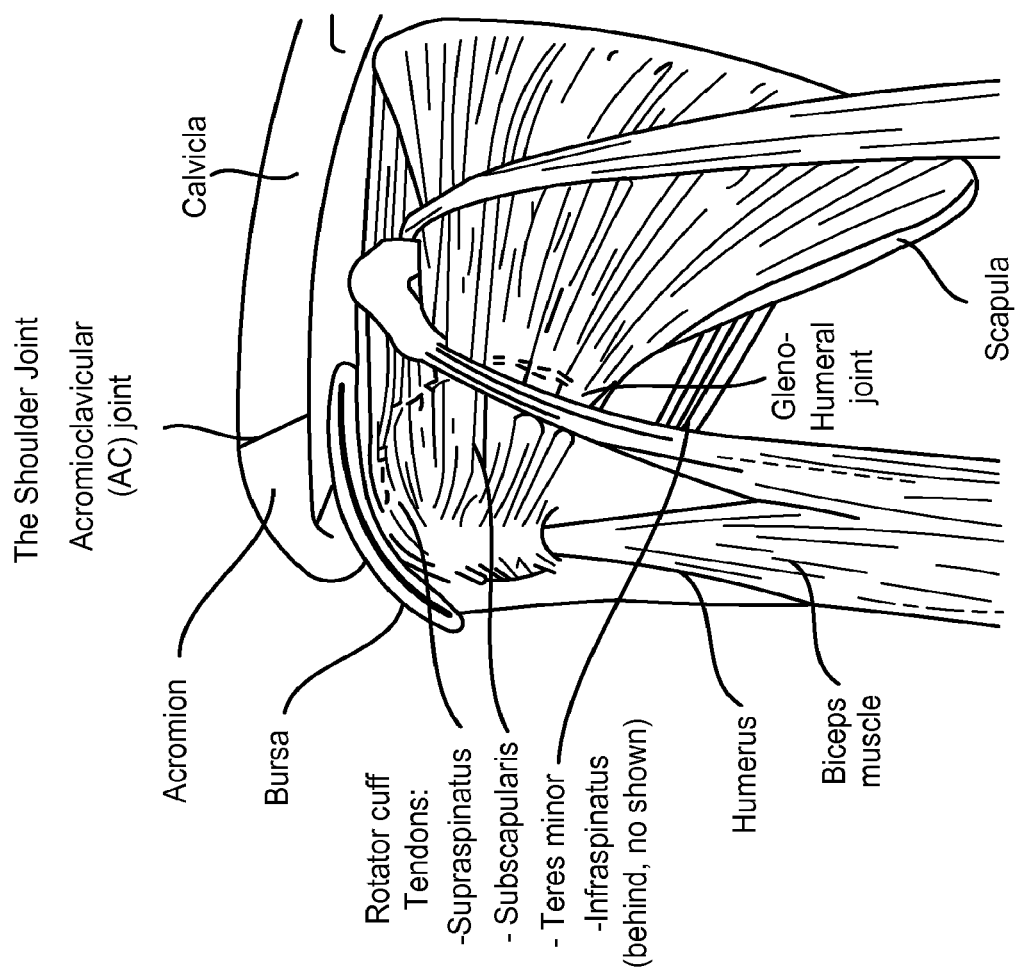
FIG. 1 shows a general view of the anatomy of a human shoulder joint.
Figure 2A:
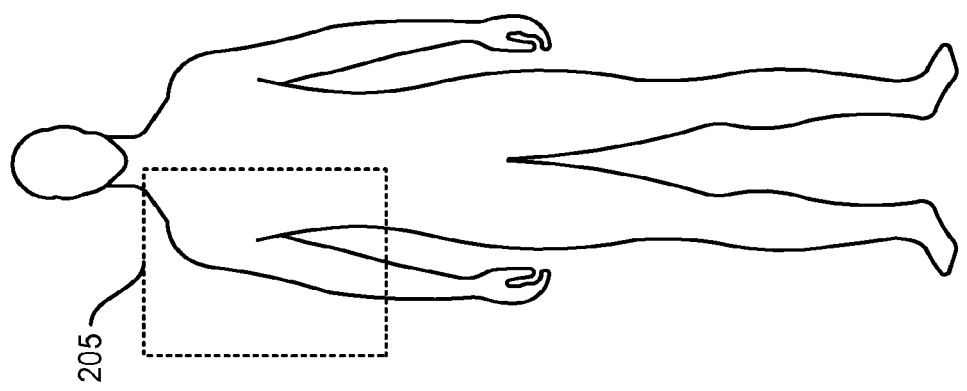
FIG. 2A shows a front of a human body.
Figure 2B:
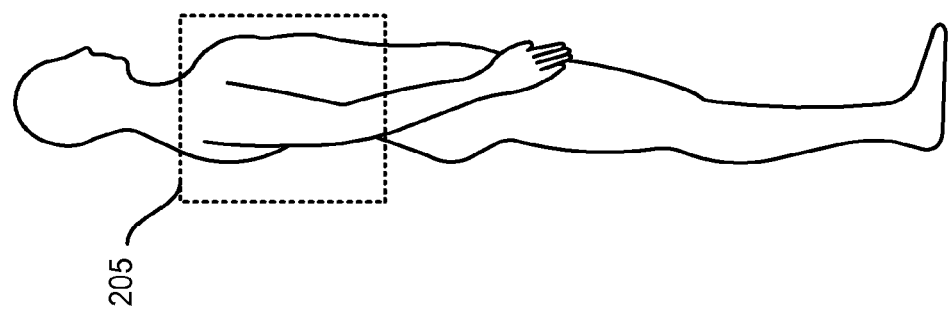
FIG. 2B shows a side of a human body.

FIGS. 2A and 2B show front and side views, respectively, of a human body. The disclosed systems and methods are particularly suited for use in a shoulder region 205 of a patient. The shoulder region 205 may vary and may include, for example, the shoulder skeletal and muscular anatomy, as well as at least portions of adjacent regions of the body including the torso and arms. In another embodiment, the systems and methods are suited for use in an anatomical region other than the shoulder region of a patient.

FIG. 3 shows a schematic representation of the overall system, which includes a shoulder monitoring system 305 communicatively coupled to a computer system 310, as described in more detail below. The overall system may also include a shoulder exostructure 315 comprised of an external structure that is passively or actively coupled to the shoulder region 205 of the patient, as also described more fully below.

The computer system 310 can include, for example, at least one computing device (such as a mobile phone, desktop or laptop computer, or Internet-based computer resource) that is communicatively coupled to the shoulder monitoring system 305 and/or the shoulder exostructure 315 (if present.) The shoulder monitoring system 305 can be connected to the other systems via a wired or wireless communication link. Moreover, the computer system 310 can be locally connected to the other systems or it may be remotely connected and/or distributed over a local area or wide area telecommunication network 320 such as the Internet. The computer system is configured to process or otherwise analyze, display, and/or archive raw and processed surface electromyography (SEMG data), rectify, filter, and integrate the data with other sensor data that is collected by the shoulder monitoring system.

In an embodiment, an enabled or authorized local or remote entity (such as a healthcare provider, a treating physician or a therapist, a payor, or a patient) can access the computer system over the telecommunication network 320.

In an embodiment, the system includes one or more wireless communication components that enable communication between components of the system and another device or just between components of the system. For example, the system can include a Bluetooth or non-Bluetooth radio chip, such as on the exoskeleton, and a non-Bluetooth radio transceiver. The radio chips can be used in place of or in parallel to a smartphone. By using an alternative or proprietary radio chip, the user is permitted to still use his/her smartphone for other uses (e.g., phone, music player or other Bluetooth application). The use of radio chips also permit patients who don't have a smartphone to use the system. Alternatively, the system may use a plug in receiver, such as a micro USB, in combination with a proprietary radio chip that attaches to a mobile phones or other user device.

The computer system 310 can be integrated with or into a mobile user device, such as a smart phone or tablet. A smart phone or the device can be sized and shaped to be positioned in a case that is also sized and shape to carry other components of the system including the exostructure 315.

With reference still to FIG. 3, the shoulder monitoring system 305 includes an embedded computer and one or more components, such as sensors, that are configured to monitor and provide feedback with respect to the shoulder region, including, for example, movement, motion, muscle activity and/or forces acting on the shoulder region. In an embodiment, the shoulder monitoring system 305 includes components of a surface electromyogram (EMG) system including one or more sensors that are positioned at predetermined locations of the shoulder region for recording the electrical activity produced by skeletal muscles. The EMG system may include an electromyograph that is part of or communicatively coupled to the computer system 310. The sensors can be attached to various portions of the system. For example, the sensors can be placed on the body or the exostructure or connect the body to the exostructure. The shoulder monitoring system may include accelerometers and neuro-feedback capability.

The feedback may be provided to the patient and/or other users in a variety of formats including audio feedback, visual feedback, tactile feedback, and data feedback that represent the user's interaction with the system. The feedback can include measurements of muscle activity relative to predetermined criteria to monitor, for example, whether a user is not using a muscle, over-using a muscle, or not meeting or not complying with recommended muscle activity or a physician prescription. In an embodiment, the system monitors muscle movement, such as with respect to predetermined levels or types of motion, and provides data as to whether the muscle movement meets predetermined criteria.

The system may also include a user interface that includes one or more mechanical or virtual input mechanisms that permit the user to control any aspect of the system. For example, the user interface can include an on/off control and a volume or mute control. The system can be configured to operate in various modes, including an off mode, a charging mode and a non-mode. The on mode can include, for example an active mode, a sleep mode, and an alarm mode. The user interface can be presented in whole or in part on any component of the system including the computer system 305.

In an embodiment, the system includes an input for a user to provide a level of pain that the user is experiencing when conducting a certain activity or in a position. The system can also include any of a variety of indicators for providing an indication to a user relating to any aspect of the system. The indicators can include visual indicators (such as lights), audible indicators, and tactile feedback indicators (such as a vibration or silent feedback element).

It should be appreciated that the forces acting on the shoulder region may vary based on the type of movement as well as the orientation of the patient's shoulder or arm relative to the patient's torso. The orientation of the patient's torso and other parts of the body relative to horizontal may also affect the forces acting on the shoulder region. Placement of the EMG sensors and motion sensors and angle measurement sensors on the shoulder region and the patient's torso can take into account movement of the shoulder during treatment as well as the orientation of portions of the body relative to one another and to the horizontal.

The overall system optionally includes the shoulder exostructure 315, which is an external structure that is positioned on the shoulder region 205 of the patient. The structure is entirely external to the body although in an alternate embodiment at least a portion of the structure extends at least partially beneath the skin of the patient in the shoulder region with a majority of the structure being external to the skin. The exostructure 315 may vary in structure and can include for example, an interlinked framework of rigid and/or malleable structural components that are attached to the body in the shoulder region. In an embodiment, the exostructure 325 is a framework formed of relatively elongated, slender pieces joined so as to surround sizable empty spaces or nonstructural panels. In another embodiment, the exostructure is a strap or band such as a sling that surrounds and/or supports the shoulder region. The exostructure can include a component that communicates with an external component either wirelessly or in a wired manner.

In an embodiment, the exostructure 315 is passively attached to the shoulder region such that the exostructure does not exert force on the shoulder region during movement or non-movement of the shoulder region. The exostructure 315 can also be configured to exert force on the shoulder region during movement or non-movement of the shoulder region. The exostructure can be configured to exert a force on the shoulder region such as by opposing movement of the shoulder region. In another embodiment, the exostructure includes a single use, flexible, bandage-like device that is adhered to the skin. The bandage-like device includes integral SEMG electrodes and batteries.

In use, the system is used as part of a regimen for treating shoulder problems. A patient can be fitted with the shoulder monitoring system, which is coupled to the computer system and possibly the exostructure. A care provider can then provide a treatment regimen to the patient, which may include prescribed movements of the shoulder region over a period of time. The system is used to monitor the patient and can be used to revise the prescribed movements based on feedback from the system. In this regard, the system can monitor and provide feedback on the following exemplary factors:

Motion monitoring: the system can be used to monitor motion of the shoulder region. For example, motion and angle measurement sensors, such as accelerometers, gyroscopes, and magnetometers are used to measure the relative motion and angle between the humerus and the scapula, between the scapula and the thorax, and between the humerus and the thorax. In an example, the shoulder monitoring system 305 includes a 3D accelerometer that is mounted on the upper arm and another mounted on the chest. The relative motion of the upper arm relative to the chest is recorded. Feedback is provided to the user, for example via audible signal, physical vibration, etc. when the motion is excessive, not sufficient, or when the motion crosses a predetermined threshold. This threshold can be manually set by the physician, therapist, or healthcare provider, and can be electronically adapted, for example changing with time after surgery, or remotely changed for example via wireless communication with a web server. Data, such as number of activity cycles, number of times threshold was exceeded, maximum motion, acceleration, etc. is recorded locally using the computer system 310, and/or transmitted to the treating physician, therapist, healthcare provider, or third party payor. In an embodiment, the system automatically transmits data and does not require user interaction or commands to transmit the data.

Muscle activity: the system can be used to monitor and record muscle of the shoulder region, for example using EMG sensors to monitor electric activity in the muscle. The monitoring of muscle activity can be important to determine if the patient is performing an appropriate exercise. This can be critical when muscle contraction is contraindicated, for example after tendon repair. In an example, feedback is provided to the user, for example via audible signal, physical vibration, etc. when the electrical activity of the muscle exceeds a predetermined threshold. This threshold can be manually set by the physician, therapist, or healthcare provider, can be electronically adapted, for example time after surgery, or remotely changed for example via wireless communication with a web server. Data, such as number of muscle contractions events, number of times threshold was exceeded, maximum electric activity, etc. is recorded on the device, and/or transmitted to the treating physician, therapist, healthcare provider, or third party payor.

External pressure: the system can be used to monitor pressure and force on the shoulder region, or equivalent sensors are used to measure the pressure between the extremities and the exostructure (such as a sling, brace, exoskeleton, or similar device.) The sensors monitor the loading shared by the supporting exostructure, and provide quantitative information as to efficacy of external support as well as provide information on whether the patient is exceeding the motion permitted by the support.

Data synthesis: The combined data from motion, muscle activity, pressure exerted, and any other data source is synthesized by the computer system 310 to provide global feedback of the activities being performed. This combination is more likely to detect adverse activities that can compromise surgical outcomes, delay recovery, or lead to complications. Further, these data coupled with appropriate outcome measures can be used to monitor and guide rehabilitation and enhance outcomes.

Example Exostructure Embodiments

Various embodiments of the shoulder exostructure structure 305 are now described. It should be appreciated that the embodiments of the exostructure described herein are non-limiting examples.

Figure 4:
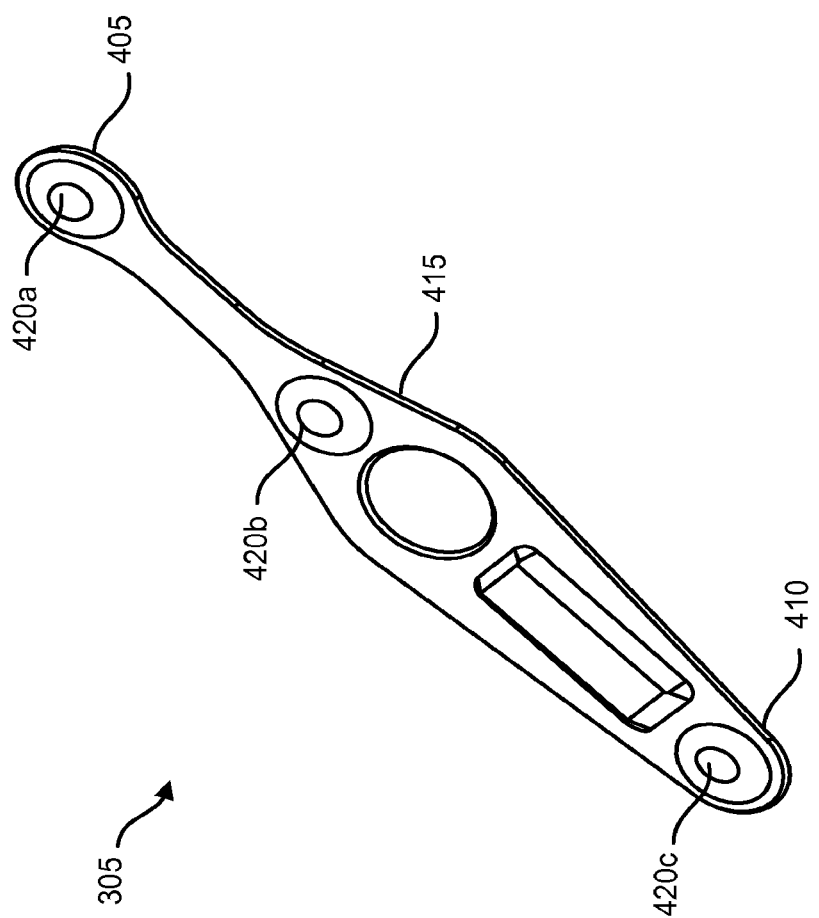
FIG. 4 shows an embodiment of an exostructure of the system.
Figure 6:
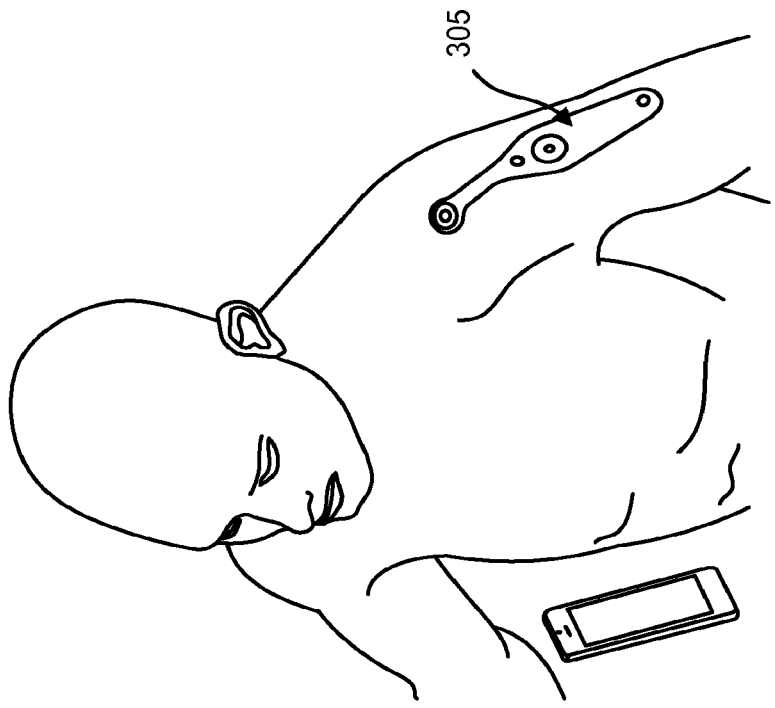
FIG. 6 shows the exostructure positioned on a shoulder region of a patient.
Figure 5:
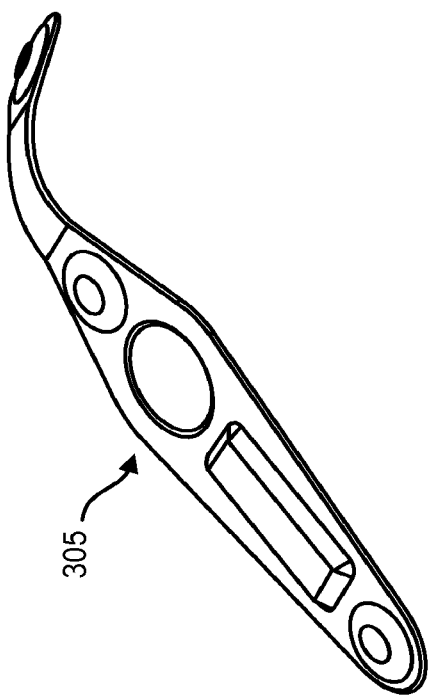
FIG. 5 shows the exostructure in a flexed state.

FIGS. 4 and 5 shows an embodiment of an exostructure 315 which is formed of an elongated body, patch or band that is sized and shaped to be positioned on the shoulder region of a patient, such as shown in FIG. 6. Any of the embodiments of the exostructure can be configured as a single use, disposable device. Or, the exostructure can be configured to be reusable in that it can be removed from the body and then replaced on the body after a period of time. The exostructure in an example embodiment can be worn for up to 3 to 7 days although the period of time for which it is used may vary.

With reference still to FIG. 4, the exostructure is formed of an elongated band of flexible material having a first end 405, a second end 410 and a center region 415. As shown in FIG. 6, the band is sized such that the first end 405 can be positioned at or near the shoulder of the patient while the second end 410 is positioned at or near an upper arm region of the patient. The band is made of a thin, flexible material that is capable of articulating along with motion of the patient's shoulder and arm such that the band is passive and does not affect or oppose motion of the patient's shoulder and arm. FIG. 5 shows a region the band bending although it should be appreciated that the band can bend along other regions other than what is shown in FIG. 5.

The band includes a front face and a rear face. The rear face of the band contacts or faces the patient's arm when worn. In this regard, at least a portion of the rear face can be equipped with an attachment element configured to secure at least a portion of the band to the patient's body. For example, the attachment element can be an adhesive or other type of element configured to attach to the patient's body. In an embodiment, the attachment element is a suction cup. In an embodiment, the adhesive is a re-positionable skin adhesive such as 3M's 2749P silicone adhesive. The Use of re-positionable adhesives allows the patient to remove the wearable patch such as for bathing/hygiene purposes. This can extend the time that a patient can wear a given device. This also allows for re-positioning for proper alignment if needed.

The band also includes one or more electrodes 420, such as electrocardiogram (ECG) electrodes, positioned at one or more locations along the band, such as on the front face of the band. In the illustrated embodiment, the band includes three electrodes 420 including a first electrode 420 a located at the first end 405, a second electrode 420 b located at the center region 415, and a third electrode 420 c located at the second end 410 of the band. The quantity and location of the electrodes 420 can vary, as described in more detail below.

The illustrated embodiment of the band 305 includes at least one opening or hole that provides visual line of sight and/or tactile access through the band to the wearer's skin when the band is positioned on the wearer. The opening can be used to align the band 305 with a landmark on the skin such as a surgical landmark including a surgical puncture. For example, the band 305 can include one or more alignment markers printed on the band 305 so that the opening serves as a receptacle. The band can also include two, three, four or more openings that are arranged in a predetermined pattern so that each opening can be aligned with a landmark on the skin for properly positioning the band 305. In user, after a surgical procedure, a user aligns the opening(s) with one or more landmarks, such as surgical puncture(s) on the skin. One or more of the openings can also have a predetermined shape that is configured to match a shape of a landmark (such as a surgical incision shape) on the skin.

Figure 14:
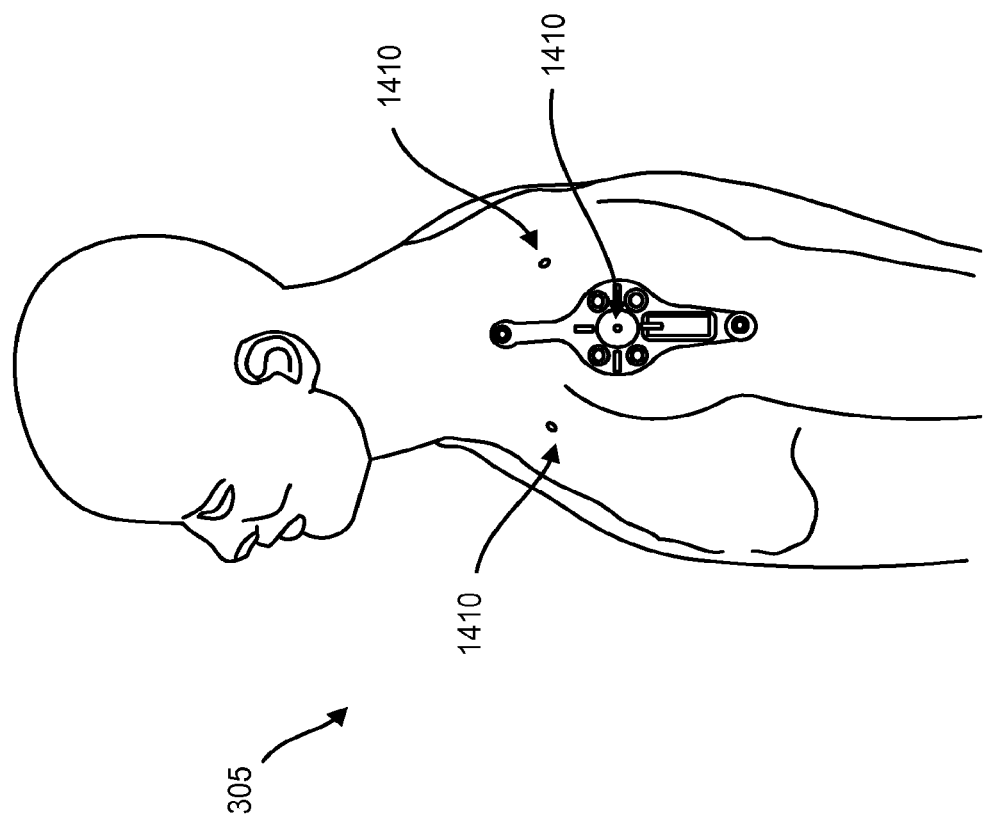
FIGS. 14-16 show additional embodiments.

FIG. 14 shows an example of such an embodiment wherein the band 305 includes alignment markers, such as reticle lines, that are positioned around an opening on the band 305. Note that one or more markings 1410 or dots, corresponding to surgical punctures, are located on the skin and can be used to align the band in conjunction with the opening(s) in the band and the marker(s) on the skin. The markings on the shoulder can be, for example, locations of arthroscopy portals (through which the scope and surgical instruments are inserted). The central circular window of the band is centered on the middle portal. The top end contains the ground electrode, which is placed on the acromion bony prominence, the arthroscopy portal window is a target for the live EMG electrodes (four electrodes around the opening), and the bottom end has an electrode that aligns with the insertion of the deltoid.

Figure 16:
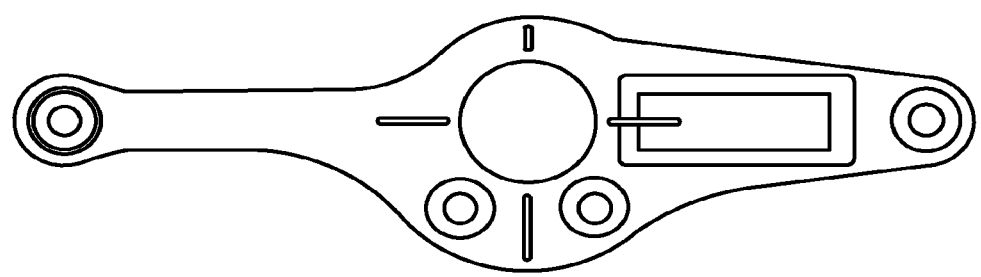
Figure 15:
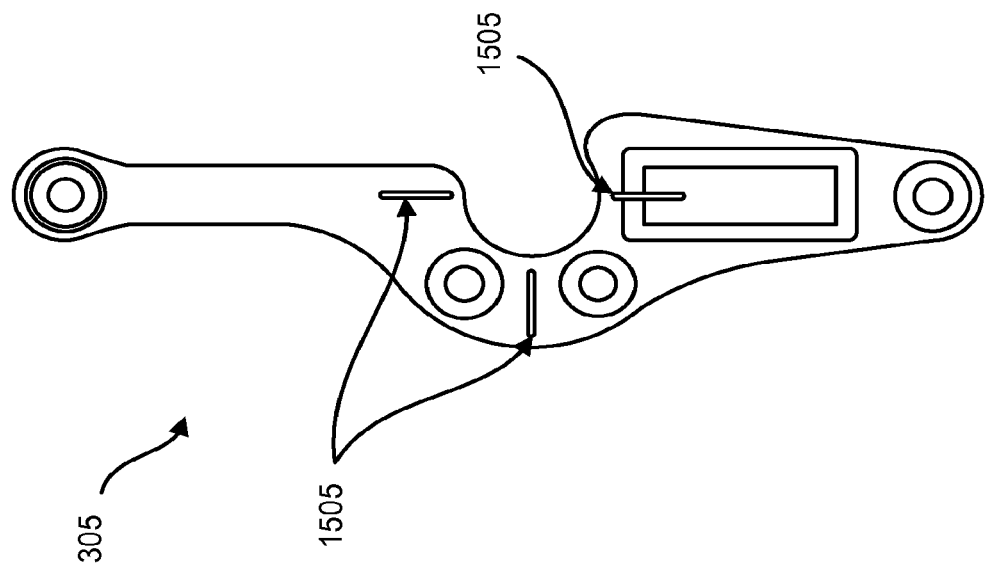

FIGS. 15 and 16 show alternate embodiments with alignment markers 1505. The bands 305 in these embodiments include a single opening or an opening that is not completely surrounded or enclosed by material as in the embodiment of FIG. 15. The embodiment of FIG. 15 can be used for monitoring two muscles or two areas of the deltoid, while the embodiments of FIGS. 16 and 17 can be used for single muscle sensing.

The opening can be fully open such that it is a hole or it can be covered with a material that permits a user to view through the opening although it is actually covered with a material.

In another embodiment, one or more alignment structures are removably attached to the band 305 and the alignment structures aid in aligning the band to a landmark on the skin. Once aligned, the alignment structures can be removed from the band.

In an embodiment, the band includes at least one electrode (referred to as a test electrode) that is configured to perform a test with respect to the other electrodes to ascertain whether the electrodes are properly functioning. For example, an operator can cause the test electrode to send an electrical signal to one or more of the other electrodes. The test electrode may send an electrical sign through the skin. The test electrode may wait a predetermined time period to receive an electrical confirmation signal from at least one of the other electrodes that the other electrode(s) received the signal. If a confirmation is not received within a predetermined time period, this may be an indication that at least one of the other electrodes has malfunctioned or that the other electrodes are not in proper contact with the skin. A signal or alarm may then be sent to the user for appropriate action.

The electrodes can be fixedly or removably attached to the band. For example, in an embodiment the electrodes are permanently mounted on the band. Such an embodiment may use a conductive interface such as a gel to enhance detection of an EMG signal. In another embodiment, the electrodes are removable and replaceable relative to the band. The band may include standard female ECG electro steps on the rear face of the band to permit a relatively quick replacement of the electrodes. The device may be powered by a rechargeable battery source. A charging station can be used as an interim data storage source which could then transmit the data to remote storage such as a web server. A user may actuate a switch or other actuator to power or energize any part of the system.

Figure 8:
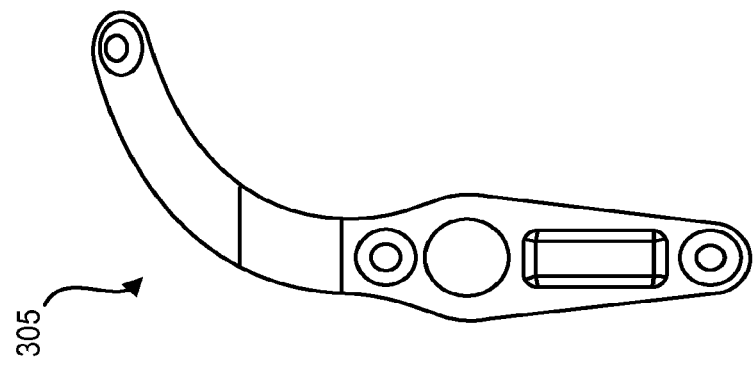
FIGS. 7 and 8 show examples of curved exostructures.
Figure 7:
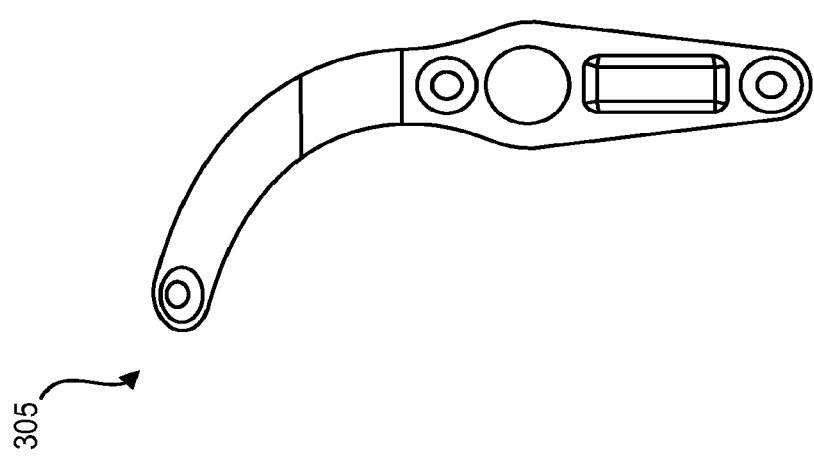

As mentioned, the electrodes can be placed at various locations on the band in order to effectuate different placements of the electrodes relative to the users body when the device is worn. In another embodiment, the band can be shaped in a manner that effectuates placement of electrodes at desired locations on the body when worn. For example, FIGS. 7 and 8 show an embodiment wherein the band as a curved upper region that curves away from a longitudinal axis of the lower region of the band. The band can have various shapes and/or contours that permit the electrodes to be selectively positioned at various locations relative to one another and relative to the patient's body.

The type of electrode can vary. In an embodiment the electrodes are standard ECG, EKG, or EEG electrodes. The electrodes may be metal electrodes that are compressible he restrained against the wearer's skin. The electrodes, when positioned against the wearer's skin can be coupled with a ventilation mechanism to minimize or eliminate the effects of sweat buildup between the electrodes and the patient's skin.

In addition to or in place of the electrodes, the exostructure 315 or any other part of the entire system can include or be coupled to any of a variety of sensors that are configured to sense information relevant to treatment of a patient. Such sensors can include, for example:

EMG, muscle activity sensors;
Accelerometers, acceleration, rotation, velocity, position sensors;
Gravity sensor, earth reference sensor;

Magnetometer, direction sensors;

Temperature sensors, such as to determine if the device being worn or to detect swelling or inflammation;

Force or pressure sensors;

Global positioning sensors (GPS);

Pulse oxygen (O2);

Heart rate sensors;

Pain Sensor;

Capacitive sensor;

Strain sensors.

The exostructure 315 or any other part of the entire system can also include or be coupled to a temperature sensor to monitor patient temperature. The temperature sensor can be used to monitor whether and when the device is being worn, such as to monitor compliance. The temperature sensor can also measure local skin temperature to monitor signs of inflammation or infection. Local skin temperature, as measured by the temperature sensor, at or near the surgical site can be compared to systemic temperature to monitor the temperature differential. The temperature sensor can also monitor local skin temperature during cryotherapy or the application of cold compresses to determine the optimum duration of application. The system can provide a warning or other signal if the local temperature falls below a desirable threshold or falls to levels that can cause tissue damage (for example frost-bite).

The temperature sensor can be integrated into any part of the system. The temperature sensor can also be coupled as a remote sensor, either hardwired or wirelessly connected. This permits a clinician to measure temperature from a remote location. In an alternate embodiment, the temperature sensor is a standalone temperature sensor that can be used for post-surgical monitoring of any site on the body.

The system can also include at least one thermal sensor that measures a thermal state of a region of the person's body where the band is positioned. The sensor can send an alarm or other signal if the thermal condition does not meet predetermined criteria, such as if the skin is too hot or too cold relative to a baseline temperature or thermal condition.

In another embodiment, the system includes or is coupled to an ultrasound sensor that is configured to monitor a thickness of local tissue. Such a sensor monitors the presence or development of swelling or inflammation by monitoring a distance from the surface of the skin to a reference surface such as a bone. An ultrasound sensor coupled with a temperature sensor can be used as a more sensitive marker of infection. The ultrasound sensor can also monitor a depth and status of underlying muscle; for example to optimize placement of skin sensors such as EMG electrodes; or to monitor a source of signals such as electrical signals from the underlying muscles.

The system can also include or be coupled to a sensor that measures bioelectric properties, such as for monitoring a status of local tissue including, for example changes in electric impedance of tissue due to swelling, inflammation, and/or inflammation. In an embodiment, the system sends a small electric current through the tissue to measure electric properties such as impedance. In another embodiment, the system measures the difference in EMG signal between two or more electrodes at different locations on the skin over the muscle. The impedance may vary with swelling/inflammation as more or less water will be present between two or more electrodes.

The sensors can be positioned individually or in bundles on the exoskeleton. For example, the device can include a single suite or bundle of sensors or a second sensor suite on the device. In the case of a shoulder use, the second suite of sensors can be positioned on top of the shoulder and provide a check or indication on the arm angle relative to the shoulder.

Figure 9B:
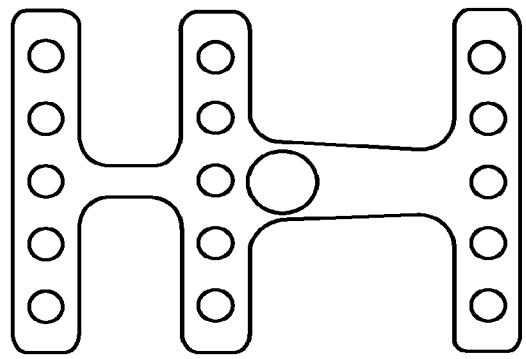
FIGS. 9A and 9B show examples of alternate shaped exostructures.
Figure 9A:
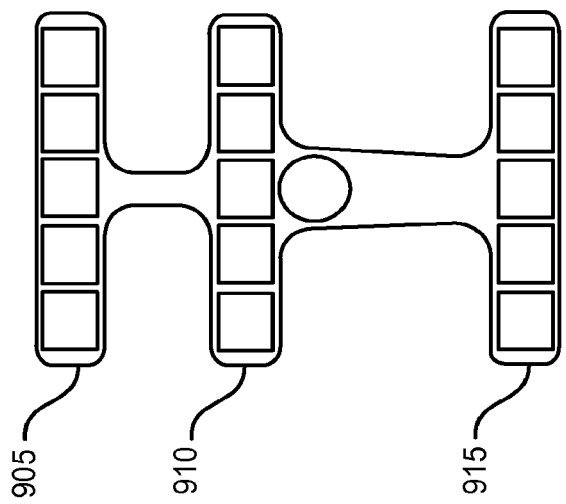

In another embodiment, shown in FIGS. 9A and 9B, the band is shaped with one or more elongated cross regions that extend laterally outward from a longitudinal axis a of the band, such as at a 90 degree angle (or other angle) relative to a longitudinal axis of the band. The cross regions provide elongated areas where one or more electrodes can be selectively positioned. In the illustrated embodiment, the band includes an upper cross region 905, a middle cross region 910, and a lower cross region. 915. The cross regions can have any of a variety of sizes and shapes that permit electrodes to be positioned at various locations on the band. The electrodes can be positioned in an array or matrix arrangement. The array can be uses to simultaneously sense multiple muscles or multiple locations on single muscle.

The band can be made of any of a variety of materials. In an embodiment, the band is formed of a durable, flexible polymer such as polyether block amide (PEBAX).

The exostructure can include its own power supply, such as a battery. In an embodiment, it includes a coin cell battery although the type of battery can vary. The battery can be a rechargeable battery. In another embodiment, the battery is capable of being inductively charged. In another embodiment, the battery is charged by attaching it to a wired connector. The battery can also be an energy harvesting battery.

Figure 10:
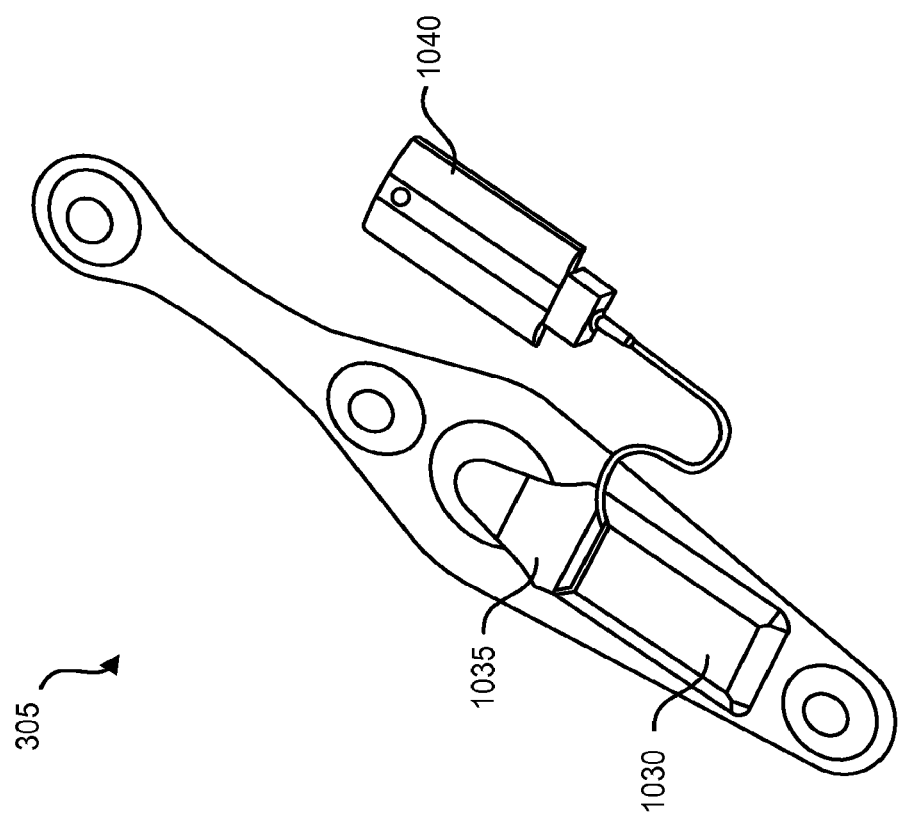
FIG. 10 shows an exostructure attached to a electrical components.

The exostructure 305 also includes one or more electronic components. The electronic components can be fixedly or removably attached to the band. In one embodiment, shown in FIG. 10, the band includes a pouch 1030 that removably contains the electronic components. The pouch 1030 can include an opening through which the electronic components can be inserted. The pouch may include a cover, such as a flap 1035, that may be opened and closed to provide access and interior of the pouch 1030. The electronic components can be removably positioned inside the pouch. In another embodiment, the electronic components are positioned inside the pouch and include a wireless or wired interface that permit the electronic components to be coupled to another electronic device 1040. A battery can also be positioned inside the pouch 1030.

In another embodiment, the electronic components are permanently mounted on the band. For example, the electronic components can be sealed in a waterproof matter within or on the band.

Figure 11:
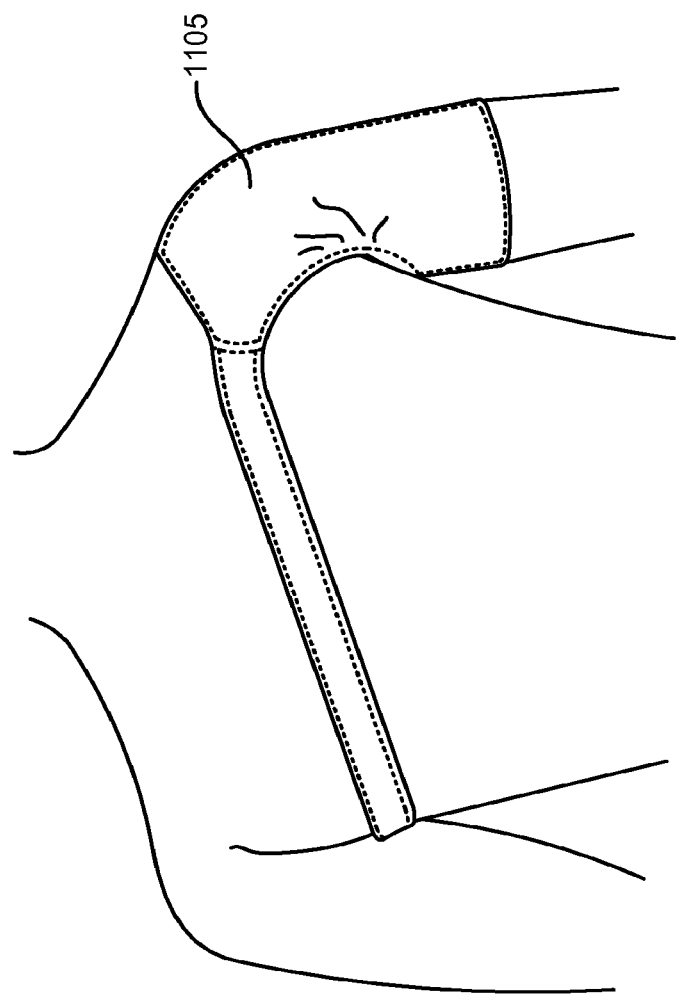
FIG. 11 shows an alternate embodiment.

FIG. 11 shows another embodiment of the exostructure where the exostructure is formed of a sleeve 1105 that is sized and shaped to fit on the shoulder region of the patient's body. In this embodiment, the exostructure does not require any adhesive as it fits over the shoulder and a compression manner. As in the previous embodiment, the electrodes are positioned on a rear face of the sleeve such that they may contact with the skin on the sleeve 1105 is worn. The electrodes can also be located inside the sleeve. In another embodiment, the sleeve includes snaps that removably attach to standard, single-use ECG electrodes.

The sleeve can be generally tubular in form such that a person installs it on his or her body by inserting the sleeve over the neck and inserting his or her arm into the tubular portion of the sleeve. In another embodiment, the sleeve is formed as a wrap with mechanical closure elements such as zippers, hook and loop couplers, or any other type of mechanical closure element.

Figure 12B:
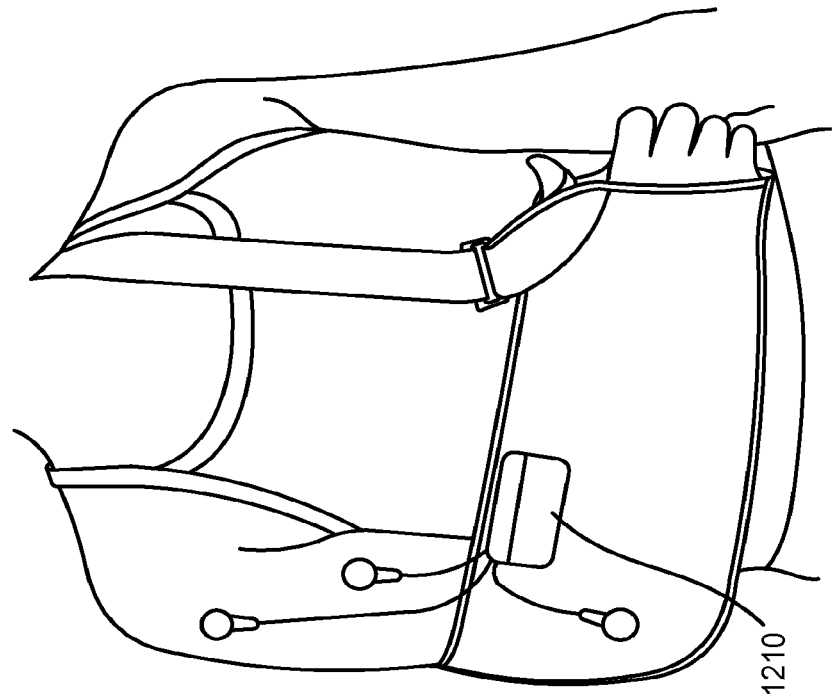
FIGS. 12A and 12B show sling embodiments of an exostructure.
Figure 12A:
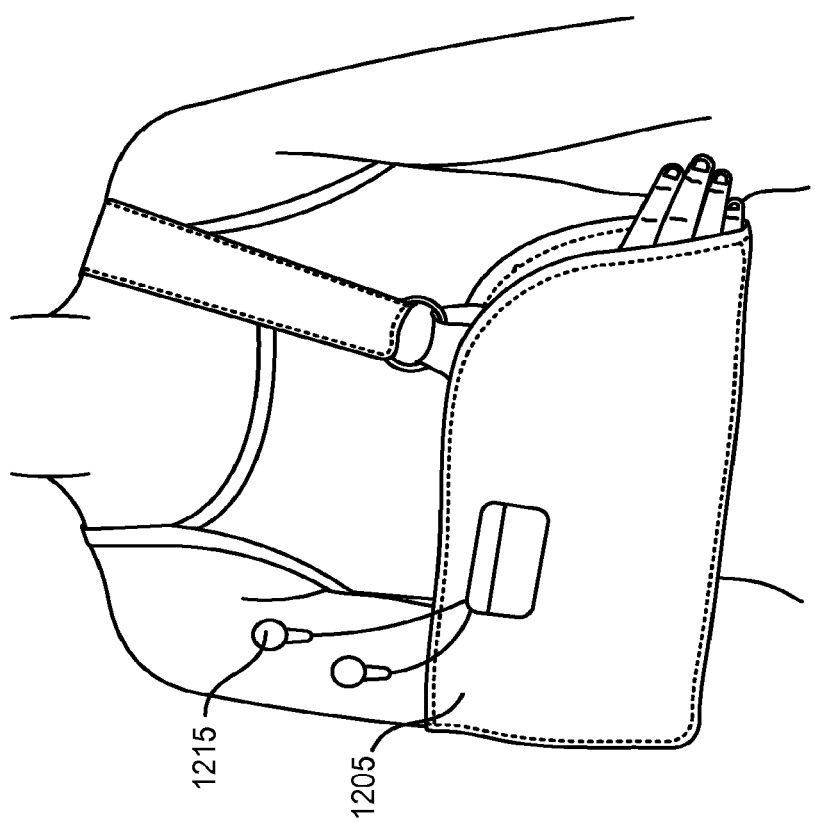

In another embodiment, shown in FIGS. 12A and 12B, the exostructure is a sling 1205 that is sized and shaped to be worn on the shoulder region of a patient's body. The sling 1205 includes a pocket 1210 in which one or more electrodes 1215 can be removably positioned. The electrodes are attached to lead wires that permit the electrodes to be attached to a patient's body at various locations. The electrodes can be sewn into or otherwise attached to the sling.

Figure 13:
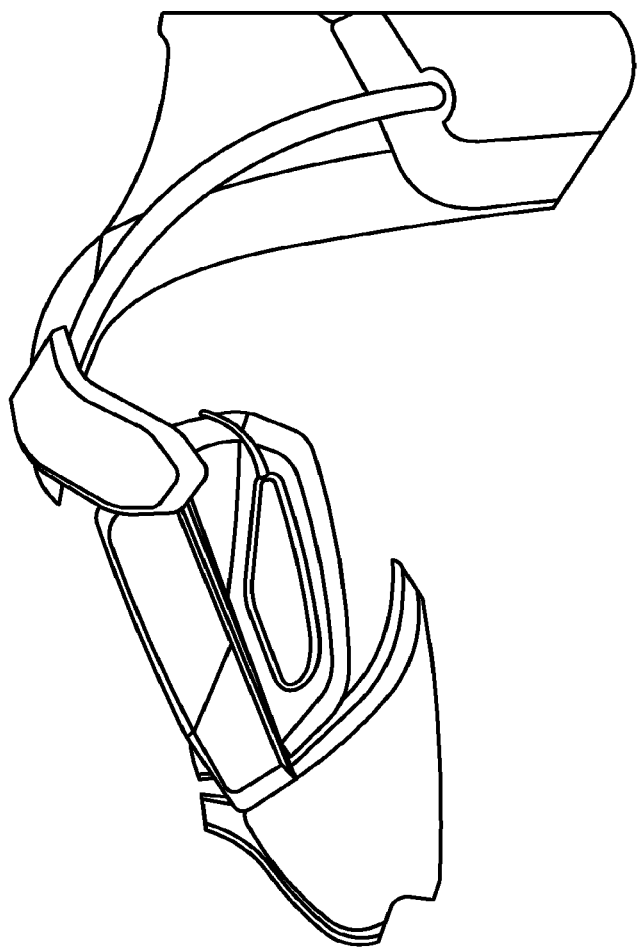
FIG. 13 shows an alternate embodiment.

In another embodiment, shown in FIG. 13, the exostructure is integrated into a mechanical assist device such as the type of device manufactured by LEVITATE.

In another embodiment, the exostructure is integrated into a shoulder wrap. In another embodiment, the exostructure is integrated with surgical dressing, bandages, etc.

It should be appreciated that the disclosed system is described in the context of use in the shoulder region although it may be configured for use in other regions of the body and pursuant to treatment regimens for various conditions or injuries. For example, the system may be configured for use with bone joint and muscle conditions, such as quad tendon or patellar ligament repair (knee); Achilles tendon repair (ankle), biceps tendon repair (elbow); wrist and finger tendon repair, etc.

Example Uses

The disclosed system can be used in a variety of methods of monitoring of muscle EMG activity in motion. This can be combined with reporting of various data to the wearer of the device or other person. For example, the data can relate to:

Enhance compliance with postoperative rehab schedules for surgery to improve outcomes;

Enhance compliance with post therapeutic (non-surgical) rehab schedules to improve outcomes;

Allow creation of single, multiple, sequential, and staged rehab schedules specific for users of the disclosed device;

Self-administered rehab directed by the disclosed device;

Accelerated rehab schedules specific to the disclosed device;

Earlier return to activities of daily living and work using monitoring provided by the disclosed device;

Creation of alternative methods of performing functional tasks through the use of the disclosed device;

Focus on muscle specific exercises (inhibit certain muscles and activate others);

Monitor muscle fiber recruitment, muscle fatigue;

Instruct postural training to relieve pain, enhance kinematics;

Construct algorithms of muscle contraction, subjective reporting and motion analysis to diagnose clinical conditions;

Construct algorithms of muscle contraction sequences and motion analysis to enhance performance;

Construct algorithms of muscle contraction sequences and motion analysis to detect alterations resulting in performance changes;

Guide and monitor training and fitness schedules;

Accumulate EMG, motion, and subjective data from multiple users to establish values that correlate with clinical outcomes and performance to define and guide rehab and performance activity;

Allow use as a diagnostic tool to determine the type, extent or disease state of a patient;

Function as secure communication media between therapist and health care provider, such as a physician;

Function to deliver electronic signature for authorization of physical therapy or rehab accessories.

The system can also be for monitoring and timing of muscle contractions. Monitoring the sequence of firing of different muscles or different bundles within the same muscle may be useful from a diagnostic perspective, for rehab advice, and perhaps even athletic performance enhancement.

One or more aspects or features of the subject matter described herein may be realized in digital electronic circuitry, integrated circuitry, specially designed ASICs (application specific integrated circuits), computer hardware, firmware, software, and/or combinations thereof. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device (e.g., mouse, touch screen, etc.), and at least one output device.

These computer programs, which can also be referred to as programs, software, software applications, applications, components, or code, include machine instructions for a programmable processor, and can be implemented in a high-level procedural and/or object-oriented programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, the subject matter described herein (such as the computer system 310) can be implemented on a computer having a computer processor and a display device, such as for example a cathode ray tube (CRT) or a liquid crystal display (LCD) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

The disclosed devices described primarily in the context of being used in the shoulder region of the patient. However it should be appreciated that the disclosed system can be configured for use in other parts of the user's body not limited to the shoulder region. For example, the system can be configured for use in a wears back, knee, hip and other uses. The system can also be configured to assist in training or performance optimization of various sports, including golf, yoga, baseball, football, swimming, running, and other sports. The system can also be used for industrial safety and productivity training, prevention of lifting injuries, and calibration setting of lift assist devices.

While this specification contains many specifics, these should not be construed as limitations on the scope of an invention that is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results.

What is claimed is:

1. A method of monitoring and providing feedback regarding a post operative recovery from surgery associated with a musculoskeletal condition of a patient when excessive muscle contraction is contraindicated, the method comprising: positioning a monitoring device on skin of the patient in a region associated with the musculoskeletal condition of the patient after surgery which addressed the musculoskeletal condition of the patient, the monitoring device comprising a patch having at least one sensor that detects muscle activity of the patient in the region;
   activating the monitoring device;
   detecting the muscle activity of the patient in the region using the at least one sensor;
   determining whether the detected muscle activity of the patient exceeds a predetermined threshold associated with the post operative recovery;
   recording a number of times that the muscle activity in the region exceeds the predetermined threshold associated with the post operative recovery; and
   providing feedback to the patient indicating that the predetermined threshold has been exceeded when it is determined that the muscle activity in the region exceeds the predetermined threshold associated with the post operative recovery, wherein exceeding the threshold a predetermined number of times indicates activity that compromises an outcome of the surgery.

2. The method of claim 1 wherein providing feedback comprises providing one or more of visual, audio, and tactile.

3. The method of claim 1 wherein detecting the muscle activity comprises detecting electrical activity produced by one or more muscles associated with the patient's musculoskeletal condition.

4. The method of claim 1 further comprising adjusting the predetermined threshold in view of improvement of the musculoskeletal condition.

5. The method of claim 1 further comprising determining the predetermined threshold based upon a level of muscle activity that will inhibit recovery.

6. The method of claim 5 wherein muscle contraction is contraindicated recovery from the musculoskeletal condition.

7. The method of claim 1 further comprising recording wherein the recording of the number of times the muscle activity exceeds the predetermined threshold is recorded in a form of data and transmitting the data.

8. The method of claim 7 wherein the data is automatically transmitted.

9. The method of claim 1 further comprising adjusting the predetermined threshold in view of a deterioration of the musculoskeletal condition.

10. A method of monitoring and providing feedback regarding muscle activity associated with a surgical repair of a musculoskeletal condition of a patient to aid a patient's post operative recovery when muscle contraction is contraindicated, the method comprising:
    positioning a monitoring device that detects the muscle activity of the patient on skin of the patient in a region associated with the musculoskeletal condition of the patient after surgery which addressed the musculoskeletal condition of the patient;
    selecting a threshold of the muscle activity to support recovery from the surgical repair,
    wherein exceeding the threshold is adverse to recovery;
    activating the monitoring device;
    the monitoring device detecting the muscle activity of the patient in the region;
    determining whether the detected muscle activity of the patient exceeds the threshold;
    recording the number of times that the muscle activity in the region exceeds the predetermined threshold associated with the post operative recovery;
    provide feedback to the patient indicating that the predetermined threshold has been exceeded when it is determined that the muscle activity in the region exceeds the threshold associated with the post operative recovery, wherein exceeding the threshold a predetermined number of times indicates activity that compromises an outcome of the surgery.

11. The method of claim 10 wherein providing feedback comprises providing one or more of visual, audio, and tactile.

12. The method of claim 11 wherein detecting the muscle activity comprises detecting electrical activity produced by one or more muscles associated with the patient's musculoskeletal condition.

13. The method of claim 10 further comprising adjusting the threshold in view of improvement of the musculoskeletal condition.

14. The method of claim 10 further comprising determining the threshold based upon a level of muscle activity that will inhibit recovery.

15. The method of claim 10 further comprising recording the muscle activity.

16. The method of claim 10 further comprising wherein recording the number of times the muscle activity exceeds the threshold is recorded in a form of data and transmitting the data.

17. The method of claim 16 wherein the data is automatically transmitted.

18. The method of claim 10 further comprising adjusting the threshold in view of a deterioration of the musculoskeletal condition.

\* \* \* \* \*